(12) United States Patent
Butani et al.

(10) Patent No.: US 10,646,178 B2
(45) Date of Patent: May 12, 2020

(54) SYSTEM AND METHOD FOR CABINET RADIOGRAPHY INCORPORATING ULTRASOUND

(71) Applicant: KUB Technologies, Inc., Stratford, CT (US)

(72) Inventors: Vikram Butani, Stratford, CT (US); Chester Lowe, Stratford, CT (US); Yan Chen, Stratford, CT (US); Roberto Velasco, Stratford, CT (US); Edwin Divakaran Maria-Selvaraj, Stratford, CT (US); Vignesh Mandalapa-Bhoopathy, Stratford, CT (US); Timothy Ely, Stratford, CT (US)

(73) Assignee: KUB TECHNOLOGIES, INC., Stratford, CT (US)

( * ) Notice: Subject to any disclaimer, the term of this patent is extended or adjusted under 35 U.S.C. 154(b) by 149 days.

(21) Appl. No.: 15/891,537

(22) Filed: Feb. 8, 2018

(65) Prior Publication Data
US 2018/0228454 A1 Aug. 16, 2018

Related U.S. Application Data

(60) Provisional application No. 62/456,652, filed on Feb. 8, 2017.

(51) Int. Cl.
| | |
|---|---|
| *A61B 6/00* | (2006.01) |
| *A61B 8/08* | (2006.01) |
| *A61B 8/00* | (2006.01) |
| *A61B 6/02* | (2006.01) |

(52) U.S. Cl.
CPC .......... *A61B 6/4417* (2013.01); *A61B 6/025* (2013.01); *A61B 6/027* (2013.01); *A61B 6/463* (2013.01); *A61B 6/466* (2013.01); *A61B 6/488* (2013.01); *A61B 6/502* (2013.01); *A61B 6/5247* (2013.01); *A61B 8/085* (2013.01); *A61B 8/0825* (2013.01); *A61B 8/4416* (2013.01)

(58) Field of Classification Search
CPC ... A61B 6/5247; A61B 8/0825; A61B 6/4417; A61B 8/4416
See application file for complete search history.

(56) References Cited

U.S. PATENT DOCUMENTS

| | | | |
|---|---|---|---|
| 2007/0213617 A1* | 9/2007 | Berman | A61B 5/0091 600/473 |
| 2009/0110152 A1* | 4/2009 | Manzke | A61B 6/107 378/195 |
| 2015/0131773 A1 | 5/2015 | Lowe et al. | |
| 2015/0221091 A1* | 8/2015 | Sugiyama | A61B 6/502 382/131 |

* cited by examiner

*Primary Examiner* — David P Porta
*Assistant Examiner* — Fani Boosalis
(74) *Attorney, Agent, or Firm* — Ziegler IP Law Group, LLC

(57) ABSTRACT

The present disclosure relates to a cabinet x-ray and ultrasound system and method for obtaining x-ray images and ultrasound images of a specimen and more specifically, a system and method including a cabinet defining an interior chamber, a display, an x-ray system and an ultrasound system.

16 Claims, 13 Drawing Sheets
(5 of 13 Drawing Sheet(s) Filed in Color)

View in Sample Chamber with Door Open with
X-ray source at position (14) Top Center FRONT VIEW INTO CABINET
Door Open Typical Example of an X-ray Cabinet System View in Sample Chamber with Door Open with
X-ray source at position (14) Top Center

**Lateral View of X-Ray Source
Mounted to Swing Arm at position (14)

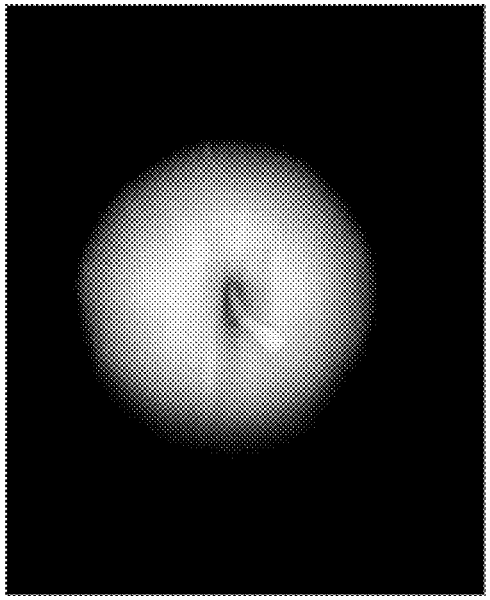
Fig. 7A - Top Slice – 59m
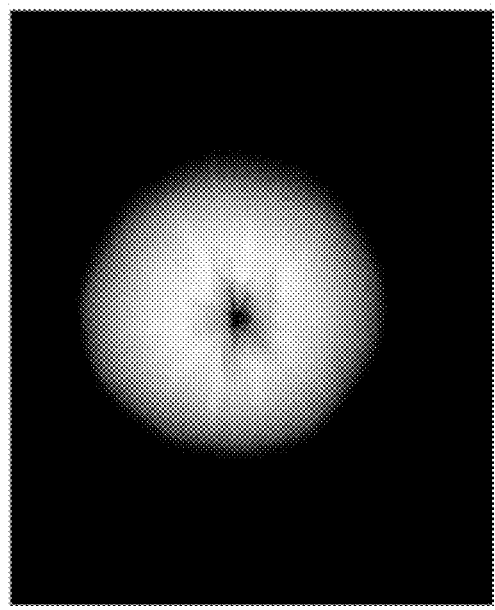
Fig. 7B - Bottom Slice – 13.5 mm
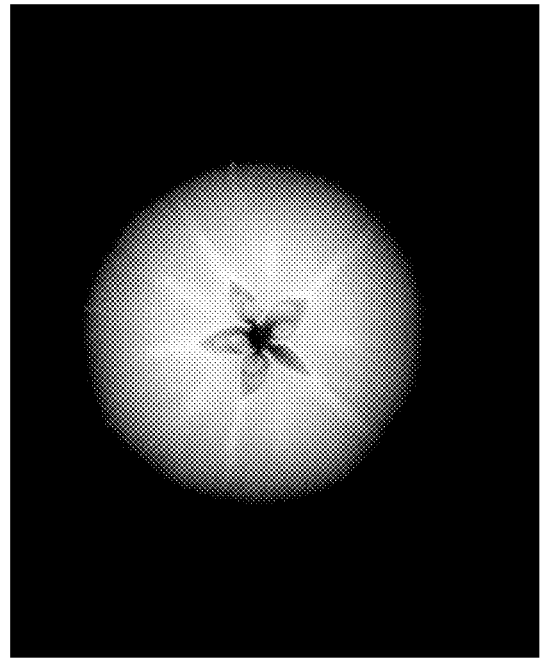
Fig. 7C - Middle Slice – 30.5 mm

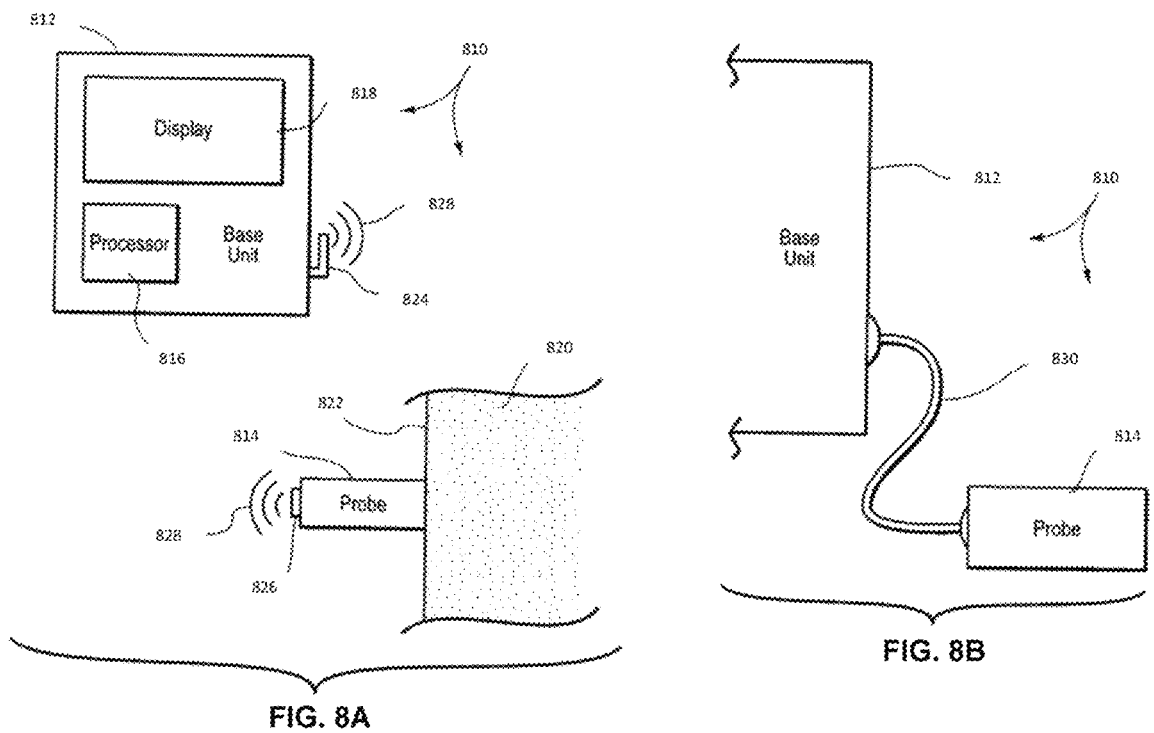
Fig. 8A and 8B - Block Diagram of Main Components including Ultrasound

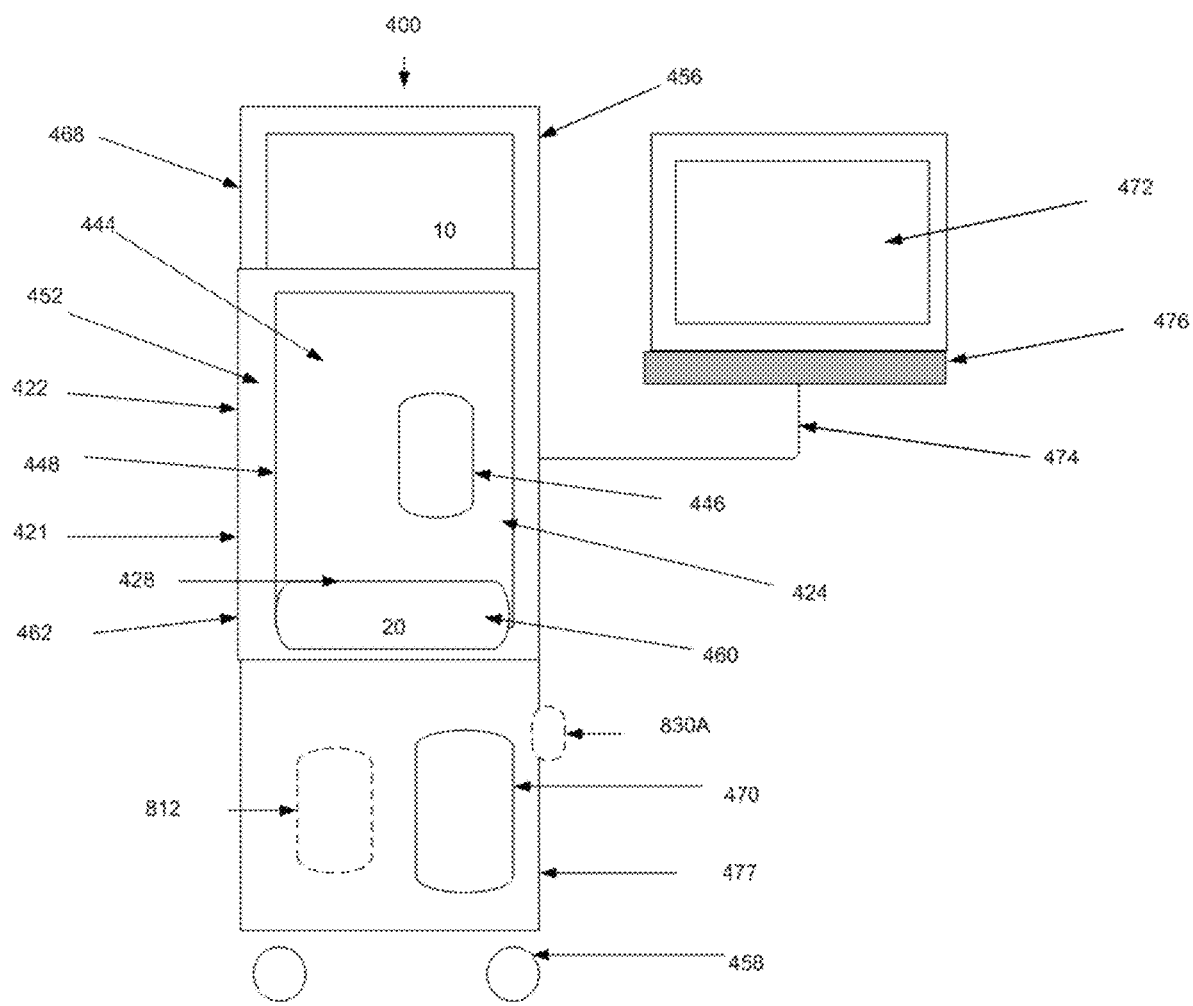
Fig. 8C – Typical Cabinet
with Processor and Connection Point

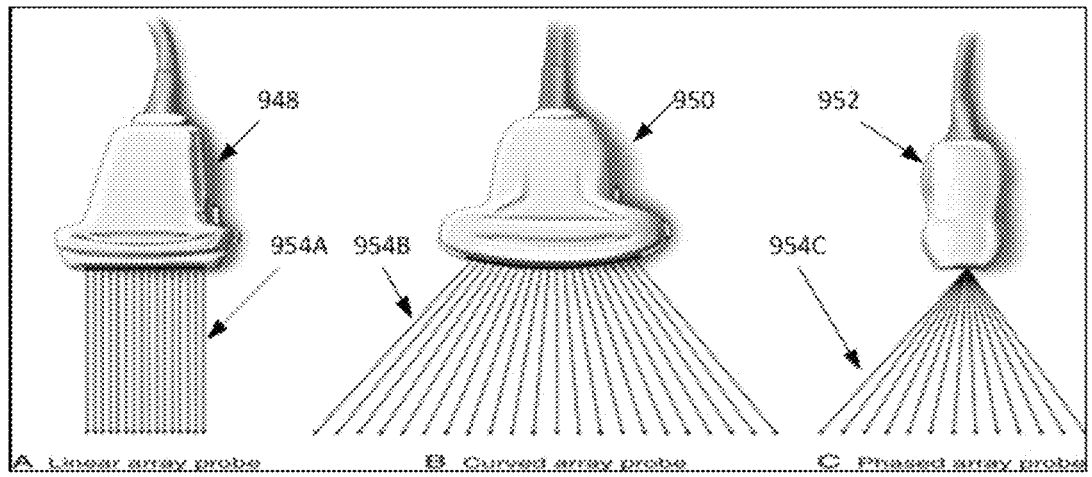
Fig. 9 – Typical Ultrasound Probes
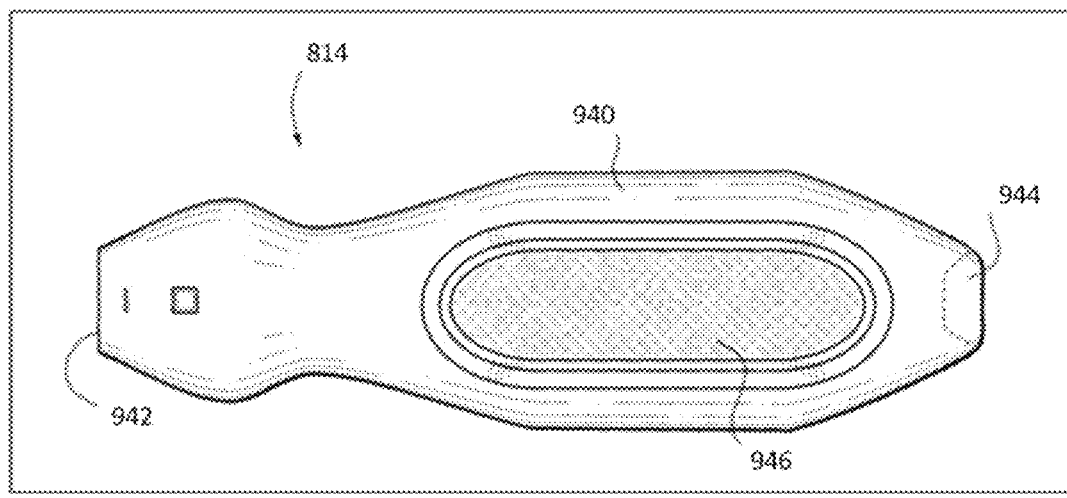
Fig. 9A – Probe Components

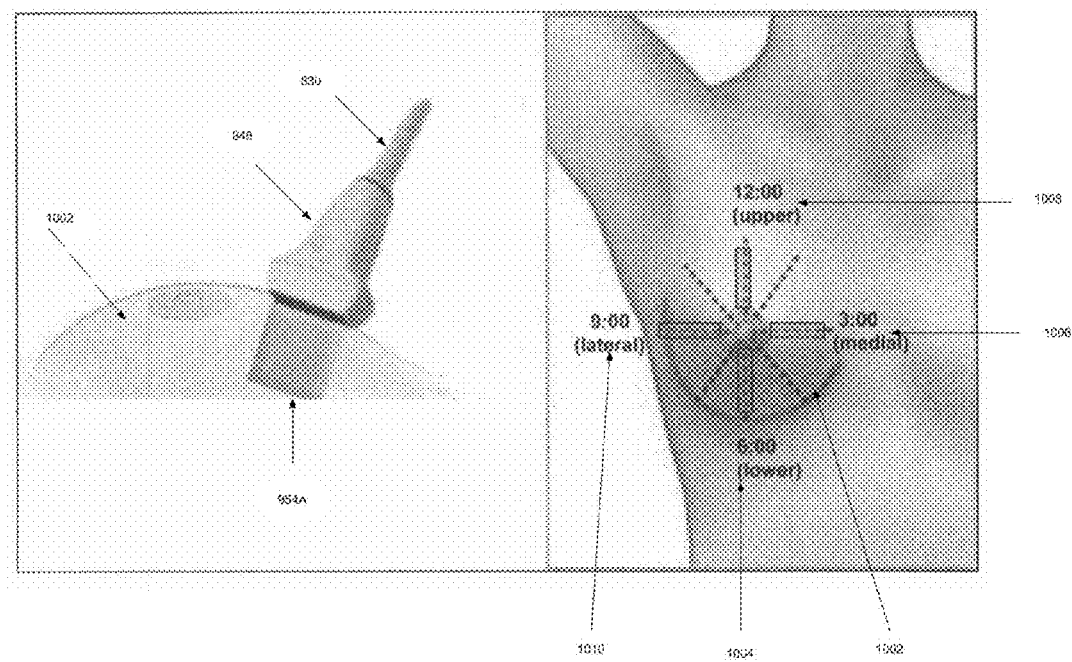
Fig. 10A-1  Fig. 10A-2
Breast Ultrasound Usage
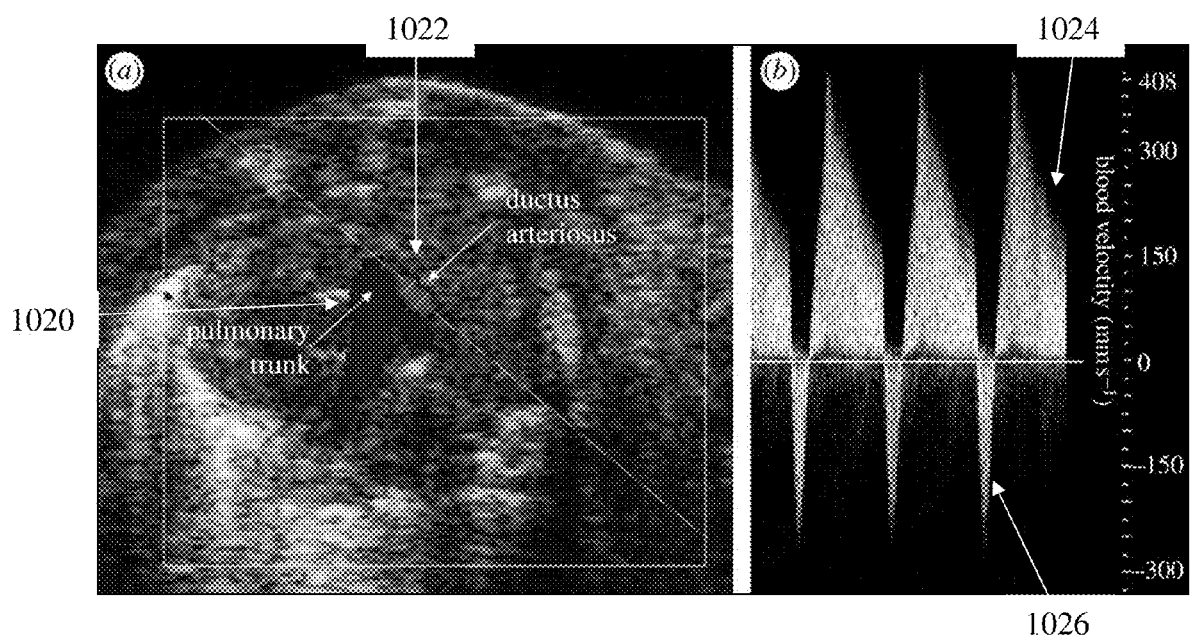
Fig. 10B(a)  Fig. 10B(b)
Breast Sonation with Highlight Breast Sonation

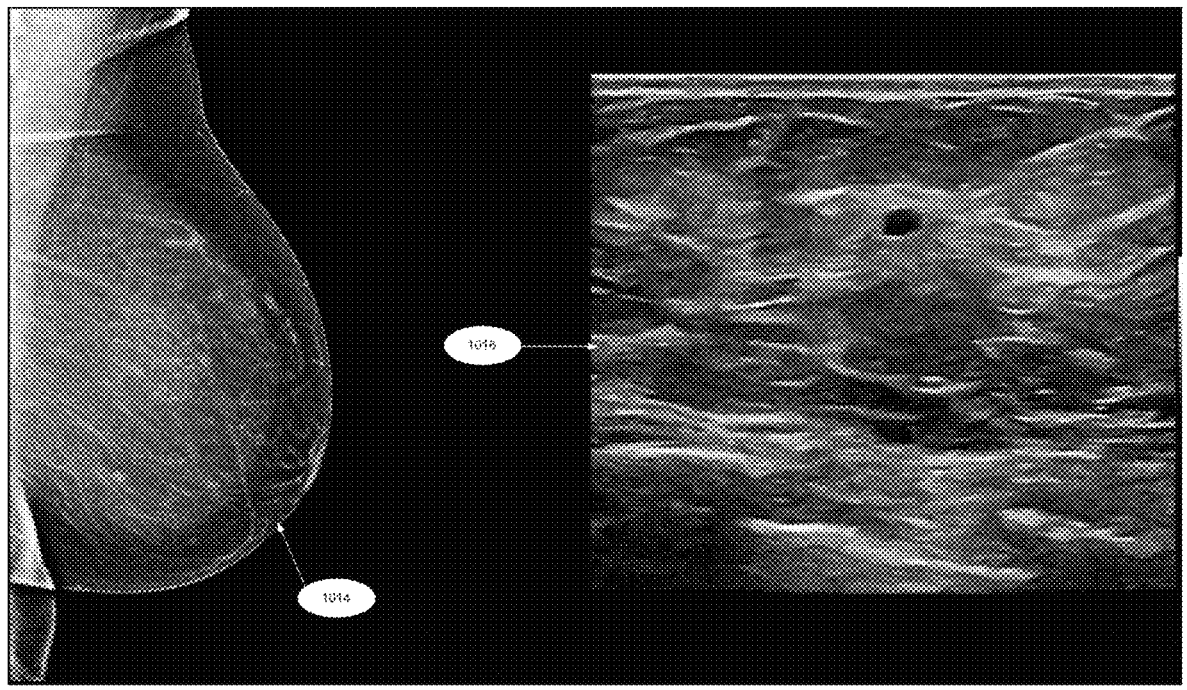
Fig. 10D – Breast Radiogram and Breast Sonation

SYSTEM AND METHOD FOR CABINET RADIOGRAPHY INCORPORATING ULTRASOUND

CROSS-REFERENCE TO RELATED APPLICATIONS

This application claims priority to and the benefit of U.S. Provisional Patent Application Ser. No. 62/456,652 filed Feb. 8, 2017, the disclosure of which is incorporated herein by reference in its entirety.

BACKGROUND

Field of the Present Disclosure

Aspects of the present disclosure relate to the field of a cabinet x-ray incorporating both radiography and wired and wireless ultrasound for the production of organic (i.e. living organisms) and non-organic (i.e. non-living organisms) images. In particular, aspects of the present disclosure relates to a method and apparatus for creating and utilizing a dual modality unit in the assistance for allowing more sensitive and reliable identification of suspicious, i.e., possibly cancerous, lesions in the case of breast specimens and the verification of the ultrasound guided interventional procedures.

Background

It would be advantageous in breast procedures due to the close proximity of instruments, lack of floor space, and furniture density to create a system and method incorporating the 2 main modalities (radiography and ultrasound) utilized in breast biopsies and surgeries for the diagnosis and verification for breast cancer. Systems for specimen radiography assist radiologists and surgeons in the detection and classification of abnormal lesions in medical images gleaned from breast biopsies/lumpectomies and an ultrasound system uses sound waves to help locate a lump or abnormality and facilitate the removal of a suspect tissue sample. It is less invasive than surgical biopsy, leaves little to no scarring and does not involve exposure to ionizing radiation.

With the utilization of a dual modality machine, the physician can use either or both modalities to detect the abnormalities, remove the abnormalities, and verify using either or both modalities that they have achieved a clean margin, for example currently 1 mm, from the cancerous or abnormal tissues and be able to visualize the resulting images on 1 video monitor instead of a multitude of video monitors which is the current state.

Currently it is believed that there is not a system or method utilizing both Ultrasound and Radiography in a cabinet system.

Today, conventional breast specimen systems can gather a digital breast specimen radiogram separately. In these systems, the radiograms of a woman's breast specimen are viewed separately for detecting suspicious lesions. Suspicious lesions are located on each image.

With a dual modality unit, the physician can utilize the ultrasound system on the patient, verify the location of the spatial markers or cancerous densities, perform the lumpectomy, and immediately transfer the excised tissue to the radiography cabinet and view the radio-opaque clip inside the cancerous tissue saving time for both the patient on the treatment table and the physician, thereby reducing cost while improving quality of care.

Breast cancer is the most common cancer among women other than skin cancer and is the second leading cause of cancer death in women after lung cancer. The American Cancer Society currently estimates that there are about 182,460 new cases of invasive breast cancer per year among women in the United States and 40,480 deaths per year from the disease. Prevention and early diagnosis of breast cancer are of foremost importance. Because early breast cancer does not produce symptoms, the American Cancer Society recommends an x-ray radiogram screening and a clinical breast examination every year for women over the age of 40. Recently, the American Cancer Society has additionally recommended an adjunctive breast MRI (magnetic resonance imaging) screening for women in certain higher-risk groups. Although the preferred embodiments described herein below are particularly applicable and advantageous for use in radiography, such as x-ray mammography and x-ray tomosynthesis breast cancer screening techniques and procedures, they are also readily applicable for other breast imaging modalities such as breast specimen radiography and digital breast specimen tomosynthesis.

Lumps or abnormalities in the breast are often detected by physical examination, x-ray mammography, ultrasound, or other imaging techniques and procedures. However, it is not always possible to tell from these imaging tests whether a growth is benign or cancerous.

A breast biopsy can be performed to remove some cells from a suspicious area in the breast and examine them under a microscope to determine a diagnosis. This can be performed surgically or, more commonly, by a radiologist using a less invasive procedure that involves a hollow needle and ultrasound-guidance. Ultrasound-guided needle biopsy is not designed to remove the entire lesion.

Ultrasound-guided biopsy can be performed by taking samples of an abnormality under some form of guidance such as ultrasound, MRI or mammographic guidance.

Specimen Radiography is considered the most cost-effective screening method for the detection of breast cancer in surgically removed breast tissue. However, the sensitivity of specimen radiography is often limited by the presence of overlapping dense fibroglandular tissue in the breast specimen. Dense parenchyma reduces the conspicuity of abnormalities and thus constitutes one of the main causes of missed breast cancer diagnosis.

About 10 to 15 percent of all screening mammograms result in a "call-back,"—i.e., the need for a further mammogram. And about 95 percent of call-backs end right there, with no further screening necessary.

The further screening can help specialists take a closer look at something to ensure accuracy of the result. The radiologist might have seen a piece of breast tissue folded over on itself, regular glandular tissue viewed from an odd angle, or something else that, with another, different mammogram, looks just fine.

But sometimes, even after a second view, something doesn't look quite right. At that point, the radiologist may order an ultrasound, a.k.a., sonogram. This call-back does not necessarily mean that the patient has cancer—or, in many cases, that the patient has anything to be concerned about. The vast majority of breast lumps, or "abnormalities" seen on mammograms, are NOT cancer. Even if the ultrasound were to prove inconclusive and you needed a biopsy, about 85 percent of biopsies are negative; no cancer. So odds are the ultrasound will show that what the radiologist saw is, in fact, not cancer at all.

But the ultrasound's main advantage over mammograms is that it's very good at showing whether a lump or mass is solid or filled with fluid. A solid lump needs further examination, either via MRI, or biopsy. But if the lump is filled with fluid, your testing is done: the lump is a cyst.

Cysts (and accompanying fibrocystic change) are quite prevalent in women under the age of 50. In fact, the most common cause of non-cancerous breast lumps in women between the ages of 30 and 50 is cysts. On an ultrasound, a cyst is dark black outlined in white; it's very distinctive, and easily identified.

An ultrasound might also show a plugged milk duct, or a fat lobule—other conditions mammograms are unable to distinguish from regular breast tissue.

A preferred embodiment system would incorporate both the Digital Breast Specimen and ultrasound systems in 1 unit to save space and real estate.

SUMMARY

As described herein, the exemplary embodiments overcome one or more of the above or other disadvantages known in the art.

The present disclosure relates to the field of a cabinet x-ray incorporating both radiography and wired or wireless ultrasound for the production of organic and non-organic images. In particular, the disclosure relates to a method and apparatus for creating and utilizing a dual modality unit facilitating a system that is more sensitive and can attain reliable identification of suspicious, i.e., possibly cancerous, lesions in the case of breast specimens and the verification of the ultrasound guided core biopsy.

A low power ultrasound system for use in sonography applications is disclosed. In one embodiment, the low power ultrasound system comprises a base unit that includes an image processor and a display. An ultrasound probe is operably connected to the base unit. The probe includes a head portion including an array of crystal transducers. A plurality of pulser/receiver modules that cause the transducers to emit ultrasonic transmit pulses are also included in the probe. The pulser/receiver modules are further configured to receive analog signals relating to ultrasonic echo receive pulses detected by the transducers. The probe includes a singular low noise amplifier that amplifies the analog signals, and an analog-to-digital converter that converts the analog signals to a digital signal. An interface is included for enabling the digital signal to be transmitted from the probe to the image processor of the base unit.

In one embodiment, the aspects of the present disclosure are directed to a cabinet x-ray system incorporating a low power ultrasound imaging device. The cabinet x-ray system incorporating a low power ultrasound imaging device includes a cabinet x-ray system, a base unit including an image processor and a display and an ultrasound probe. The base unit including an image processor. The ultrasound probe operably connected to the base unit, the probe includes a head portion including a crystal transducer array, a plurality of pulser/receiver modules that cause the transducer array to emit a plurality of ultrasonic transmit pulses, the pulser/receiver modules configured to receive analog signals relating to ultrasonic echo receive pulses detected by the transducer array, a single low noise amplifier that amplifies the analog signals, a single analog-to-digital converter that converts the analog signals to a digital signal, a processing unit that controls the pulser/receiver modules and the analog-to-digital converter, the pulser/receiver modules causing the transducer array to fire and re-fire the plurality of transducers at the target object and to receive data by only one transducer of the plurality of transducers sequentially until the target object is scanned and an interface for enabling the digital signal to be transferred from the ultrasound probe to the image processor of the base unit. The ultrasound probe may further include a multiplexer that combines the analog signals before the analog signals are amplified by the low noise amplifier. The ultrasound probe may also include a battery for providing power to components of the ultrasound probe. The interface may also include a wireless interface, and wherein the base unit includes a wireless interface. The wireless interface of the ultrasound probe and the base unit may communicate via a wireless data transfer protocol. The interface may include a cable interface between the ultrasound probe and the base unit. The low noise amplifier may produce a differential output of amplified analog signals. The ultrasound probe processing unit may control a field-programmable gate array and the interface of the ultrasound probe. The base unit may be a computer, for example, a laptop computer.

In another embodiment, the aspects of the present disclosure are directed to a cabinet x-ray and ultrasound system for obtaining x-ray images and ultrasound images of a specimen. The system includes a cabinet defining an interior chamber, a display, an x-ray system and an ultrasound system. The x-ray system includes an x-ray source, an x-ray detector, a specimen platform and a controller, the controller configured to selectively energize the x-ray source to emit x-rays through the specimen to the x-ray detector, control the x-ray detector to collect a projection x-ray image of the specimen when the x-ray source is energized and selectively display the x-ray image on the display. The ultrasound system includes a probe configured to transmit an ultrasound wave and receive sonographic data in response to the transmitted ultrasound wave and an ultrasound base unit in communication with the probe and including a processor, the processor configured to receive the sonographic data from the probe and perform image processing functions on sonographic data to collect an ultrasound image and selectively display the ultrasound image on the display.

In another embodiment, the aspects of the present disclosure are directed to a cabinet x-ray and ultrasound system for obtaining x-ray images, projection x-ray images, reconstructed tomosynthetic x-ray images and ultrasound images of a specimen. The system includes a cabinet defining an interior chamber and an equipment enclosure, a display, an x-ray system and an ultrasound system. The x-ray system includes an x-ray source positioned in the interior chamber, an x-ray detector positioned in the interior chamber, a specimen platform positioned in the interior chamber and which is a protective cover of and in physical contact with the x-ray detector and a controller, the controller configured to selectively energize the x-ray source to emit x-rays through the specimen to the x-ray detector at selected positions of the x-ray source relative to the specimen such that the isocenter of the emitted x-rays at the selected positions is located at a surface of the x-ray detector, control the x-ray detector to collect a projection x-ray images of the specimen when the x-ray source is energized at the selected positions, wherein one of the projection x-ray images is a two-dimensional x-ray image taken at standard imaging angle of approximately 0°, create a tomosynthetic x-ray image reconstructed from a collection of projection x-ray images, process the collection of the projection x-ray images in the controller into one or more reconstructed tomosynthetic x-ray images representing a volume of the specimen and relating to one or more image planes that are selectively the same or different from that of the two-dimensional x-ray image and selectively display the two-dimensional x-ray image on the display and the one or more reconstructed tomosynthetic x-ray images. The ultrasound system includes a probe configured to transmit an ultrasound wave and receive sonographic data in response to the transmitted ultrasound wave and an ultrasound base unit positioned in the equipment enclosure and in communication with the probe and including a processor and a display driver, the processor configured to receive the sonographic data from the probe and perform image processing functions on sonographic data to collect an ultrasound image, the display driver configured to receive the ultrasound image from the processor and send it to the controller, the controller configured to selectively display the ultrasound image on the display.

In another embodiment, the aspects of the present disclosure are directed to a method for obtaining an x-ray image and an ultrasound image of a specimen in a cabinet x-ray and ultrasound system, processing and displaying the x-ray image and ultrasound image of the specimen. a cabinet defining an interior chamber, a display, an x-ray system and an ultrasound system. The x-ray system includes an x-ray source, an x-ray detector, a specimen platform and a controller, the controller configured to selectively energize the x-ray source to emit x-rays through the specimen to the x-ray detector, control the x-ray detector to collect a projection x-ray image of the specimen when the x-ray source is energized and selectively display the x-ray image on the display. The ultrasound system includes a probe configured to transmit an ultrasound wave and receive sonographic data in response to the transmitted ultrasound wave and an ultrasound base unit in communication with the probe and including a processor, the processor configured to receive the sonographic data from the probe and perform image processing functions on sonographic data to collect an ultrasound image and selectively display the ultrasound image on the display. The method includes controlling the x-ray detector to collect an x-ray image of the specimen when the x-ray source is energized, controlling the ultrasound system to transmit an ultrasound wave and receive sonographic data in response to the transmitted ultrasound wave and processing the sonographic data to collect an ultrasound image and selectively displaying at least one of the x-ray image and the ultrasound image on the display.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

To further clarify the above and other advantages and features of the present disclosure, a more particular description of the disclosure will be rendered by reference to specific embodiments thereof that are illustrated in the appended drawings. It is appreciated that these drawings depict only typical embodiments and are therefore not to be considered limiting of its scope. Aspects of the present disclosure will be described and explained with additional specificity and detail through the use of the accompanying drawings in which:

FIGS. 7A, 7B and 7C—Displays the results of the imaging of an apple at multiple depth cuts after tomosynthesis reconstruction in a cabinet x-ray system incorporating aspects of the present disclosure.

FIG. 8A schematically illustrates an ultrasound system configured in one embodiment of a system incorporating aspects of the present disclosure;

FIG. 8B schematically illustrates an ultrasound system configured in another embodiment of a system incorporating aspects of the present disclosure;

FIG. 8C displays other embodiments of an x-ray Cabinet System incorporating aspects of the present disclosure;

FIG. 9 displays of various embodiments of ultrasound probes incorporating aspects of the present disclosure that can be employed in connection with ultrasound system embodiments of the present disclosure;

FIG. 9A displays another embodiment of an ultrasound probe that can be employed in connection with the ultrasound system embodiments of the present disclosure;

FIGS. 10A1 and 10A2 are examples of usage of ultrasound probes that can be employed in connection with the ultrasound system embodiments of the present disclosure;

FIGS. 10B(a), 10B(b), 100(a) and 100(b) display the results of ultrasound sonation utilizing an ultrasound probe that can be employed in connection with the ultrasound system embodiments of the present disclosure: and FIG. 10D displays radiographic image data and ultrasound sonation image data simultaneous displayed in one embodiment of a system incorporating aspects of the present disclosure.

DETAILED DESCRIPTION

The systems and methods of the present disclosure address the needs of the art by providing tomosynthesis apparatus and techniques for imaging breast specimens that overcome the shortfall of the data received from two-dimensional imaging systems. The aspects of the present disclosure enable the use of tomosynthesis to efficiently provide accurate three-dimensional imaging of a specimen in which overlapping images having differing attenuation characteristics by applying a three-dimensional reconstruction algorithm all in an x-ray cabinet.

As used herein, the term "computer," "computer system", or "processor" refers to any suitable device operable to accept input, process the input according to predefined rules, and produce output, including, for example, a server, workstation, personal computer, network computer, wireless telephone, personal digital assistant, one or more microprocessors within these or other devices, or any other suitable processing device with accessible memory.

The term "computer program" or "software" refers to any non-transitory machine-readable instructions, program or library of routines capable of executing on a computer or computer system including computer readable program code.

Digital breast specimen tomosynthesis as exhibited in U.S. Pat. No. 2015/0131773 (U.S. Pat. No. 9,138,193), Lowe, et al., entitled "SPECIMEN RADIOGRAPHY WITH TOMOSYNTHESIS IN A CABINET," the disclosure of which is hereby incorporated by reference in its entirety in the present application, where aspects of the latter may reduce the camouflaging effects of dense breast tissue and improve the sensitivity of specimen radiography for breast cancer detection in dense breasts.

Reference will now be made to figures wherein like structures will be provided with like reference designations. It is understood that the drawings are diagrammatic and schematic representations of exemplary embodiments of the present disclosure and are not limiting nor are they necessarily drawn to scale.

Specimen Tomography is a three-dimensional specimen imaging system. It involves acquiring images of a sample at multiple viewpoints, typically over an arc or linear path. The three-dimensional image is constructed by the reconstruction of the multiple image data set.

Figure 1:
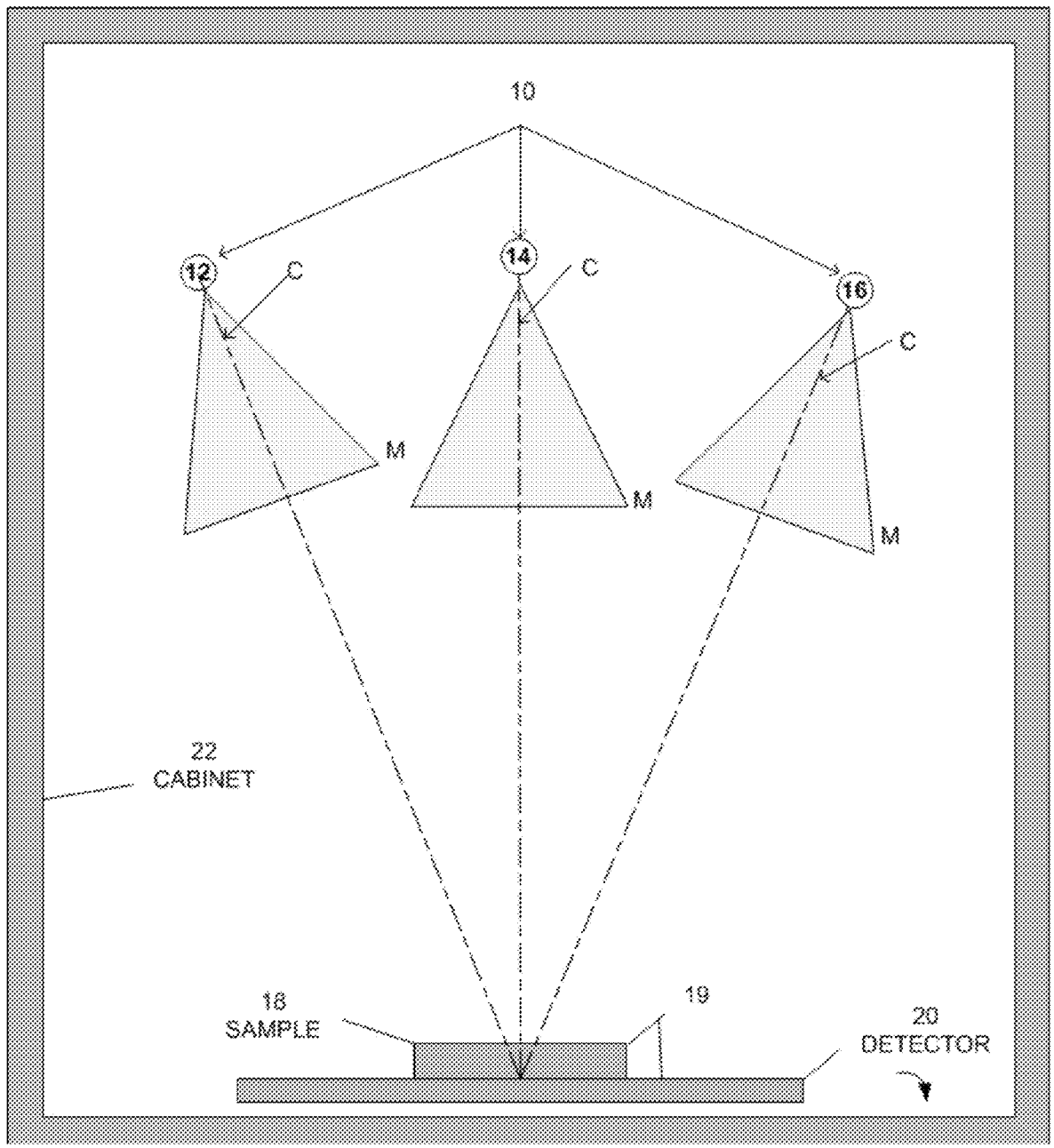
FIG. 1—Schematically illustrates a front view of an x-ray source, a specimen/sample, and a digital detector, where the x-ray source moves relative to the specimen for imaging the specimen at different angles, in one embodiment of a system incorporating aspects of the present disclosure.

One embodiment of a system 100 incorporating aspects of the present disclosure is illustrated in FIG. 1 The system 100 is totally enclosed or housed in an x-ray cabinet 22. In accordance with the aspects of the disclosed embodiments, the x-ray source 10 moves around the stationary sample, 18, typically, but not necessarily, in an arc. References 12, 14, and 16 of FIG. 1 illustrate exemplary positions of the x-ray source 10 within the x-ray cabinet 22. The reference "C" at each of the positions 12, 14, 16 of the x-ray source 10 in FIG. 1 refers to the point source of the x-ray beam. The reference "M" refers to the spread or fan of the x-ray beam.

While the detector 20 may move or rotate, in accordance with one aspect of the present disclosure, the detector 20 remains stationary relative to the sample 18 and x-ray source 10 to maintain an equidistant center point. The x-ray data taken at each of a number of exemplary positions 12, 14, 16 of the x-ray source 10 relative to the sample 18 within the x-ray cabinet 22 is processed to form images, where two or more of the differing image positions are utilized to form a digital tomosynthesis image.

In one embodiment, the aspects of the present disclosure limit the arc or linear travel of the x-ray source 10 over about a 20° to about a 50° arc, preferable about 30°, more preferable 20°. The movement can be clockwise or counter clockwise along a path, which includes for example, one or more, or a combination thereof, of the following exemplary ranges: between approximately 350° (reference position 12) to 0° (reference position 14) to 10° (reference position 16), or between approximately 340° (reference position 12) to 0° (reference position 14) to 20° (reference position 16) and or between approximately 335° (reference position 12) to 0° (reference position 14) to 25° (reference position 16). The ranges recited herein are intended to be approximate and inclusive of start and endpoints. In the example of FIG. 1 the detector 20 is stationary as is the sample 18. The sample 18 also referred to as the "object" or "imaging object" is disposed on or rests on the specimen platform 19 (which is a protective cover) or other surface of the detector 20.

In operation, source 10 is energized to emit an x-ray beam, generally throughout its travel along one or more of the paths or positions described above. The x-ray beam travels through the sample 18 to the detector 16 and the multiple images collected at varying angles are stored and then utilized for the tomosynthesis reconstruction. The x-ray source 10 may range from about 0 kVp to about 90 kVp, preferably a 50 kVp 1000 μa x-ray source.

Different embodiments of the present disclosure can utilize different ranges of motion of one or more of the x-ray source 10 and detector 20 as well as changing the angularity of one or both. The inventive aspects of the present disclosure differ from the prior art in that in prior art systems either the detector and x-ray source 10 and/or the isocenter is above the sample and not at the detector surface. In accordance with the aspects of the present disclosure, in one embodiment, the x-ray source 10 is configured to move, as described herein, while the detector is configured to remain stationary or in a fixed position.

The detector 20 and associated electronics generate image data in digital form for each pixel at each of the angular positions, 12, 14, 16 of x-ray source 10 and translations positions of the detector 20 relative to the sample 18. While only three positions 12, 14, 16 are illustrated in FIG. 1, in practice more images are taken at differing angles. For example, in one embodiment, images can be taken at approximately every 1° of rotation or motion of source 10.

Figure 2:
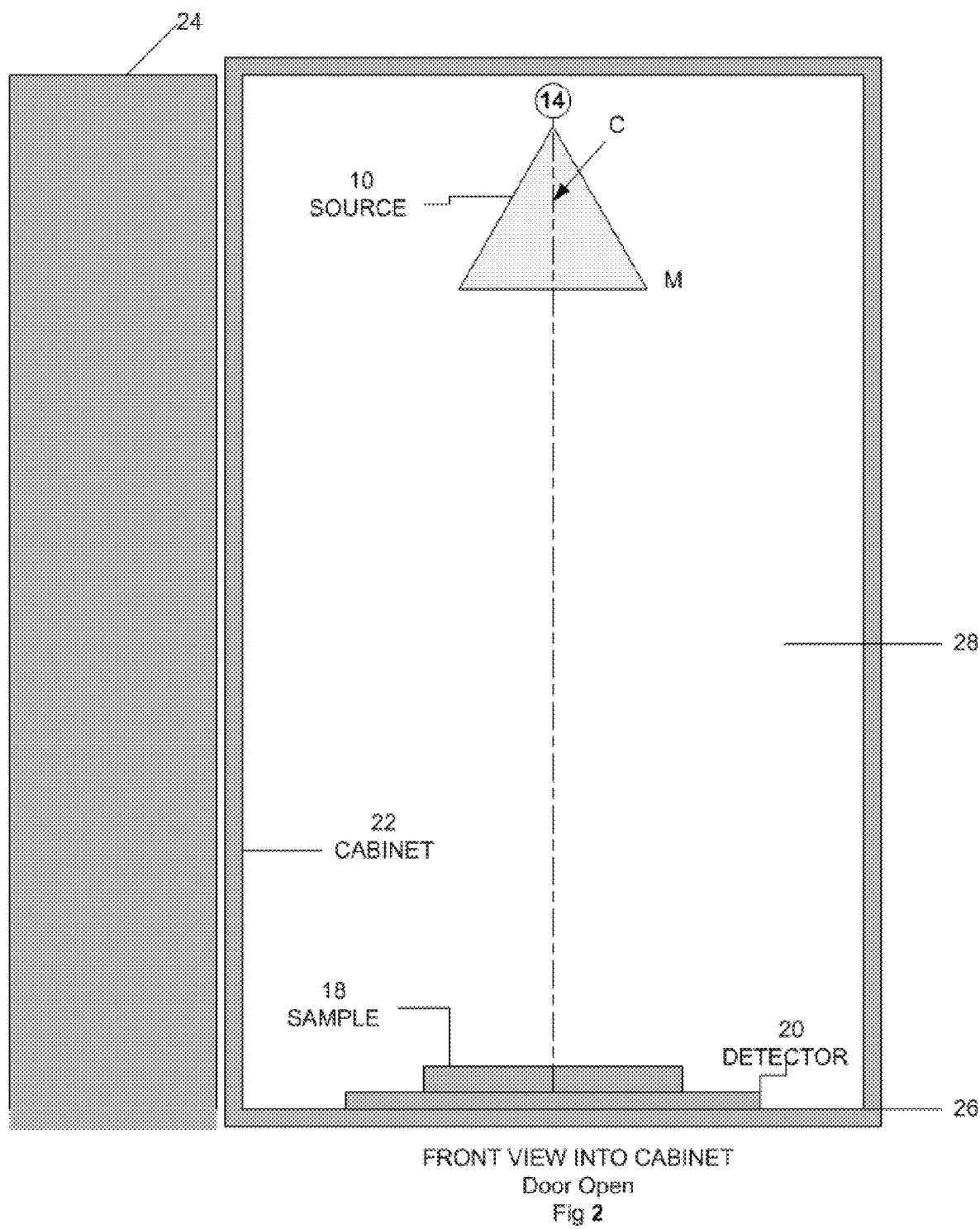
FIG. 2—Schematically illustrates an exemplary orientation of the x-ray source, specimen, and digital detector as viewed when the door of the cabinet is open, in one embodiment of a system incorporating aspects of the present disclosure.

FIG. 2 schematically illustrates one embodiment of the orientation of the x-ray source 10 as seen when the door 24 is opened and the x-ray source 10 is locate at approximately 0°, reference point 14 in this example, within the x-ray cabinet 22. In this embodiment, the motion of the x-ray source 10 can generally occur from the back to the front of the x-ray cabinet 22 with the detector 20 oriented, or otherwise disposed, at the base 26 of the x-ray cabinet 22, within the x-ray cabinet chamber 28. In one embodiment, the detector 20 is suitably coupled to the base 26 of the x-ray cabinet 22. The x-ray spread in this example can be from about 0 kVp to about 50 kVp with the system preferably utilizing an AEC (Automatic Exposure Control) to ascertain the optimal setting to image the object or sample 18 being examined.

In one embodiment, the detector 20, x-ray source 10, and the swing arm 60 (FIG. 5) servo mechanism are controlled via a combination of one or more of software and hardware, such as non-transitory machine-readable instructions stored in a memory that are executable by one or more processors. On example of such a configuration can include controller cards of a computer 470 (FIG. 4), such as a MS Windows based computer. In one embodiment, non-transitory machine-readable instructions being executed by one or more processors of the computer 470 is utilized to compile data received from the detector 20 and present resulting images to a suitable display or monitor 472 (FIG. 4) at each imaging position, such as positions 12, 14 and 16 shown in FIG. 1, the detector 20 generates the respective digital values for the pixels in a two-dimensional array. The size of detector 20 may range, for example, from about 5.08 centimeters by 5.08 centimeters to about 40.64 centimeters by 40.64 centimeters, preferably about 12.7 centimeters by 15.24 centimeters. In one example, detector 20 has a rectangular array of approximately 1536×1944 pixels with a pixel size of 74.8 micrometers. The image dataset attained at each respective position may be processed either at the full spatial resolution of detector 20 or at a lower spatial resolution by overlapping or binning a specified number of pixels in a single combined pixel value.

For example, if we bin at a 2×2 ratio, then there would be an effective spatial resolution of approximately 149.6 micrometers. This binning may be achieved within the original programming of the detector 20 or within the computer 470 providing the tomosynthetic compilation and image.

Figure 3:
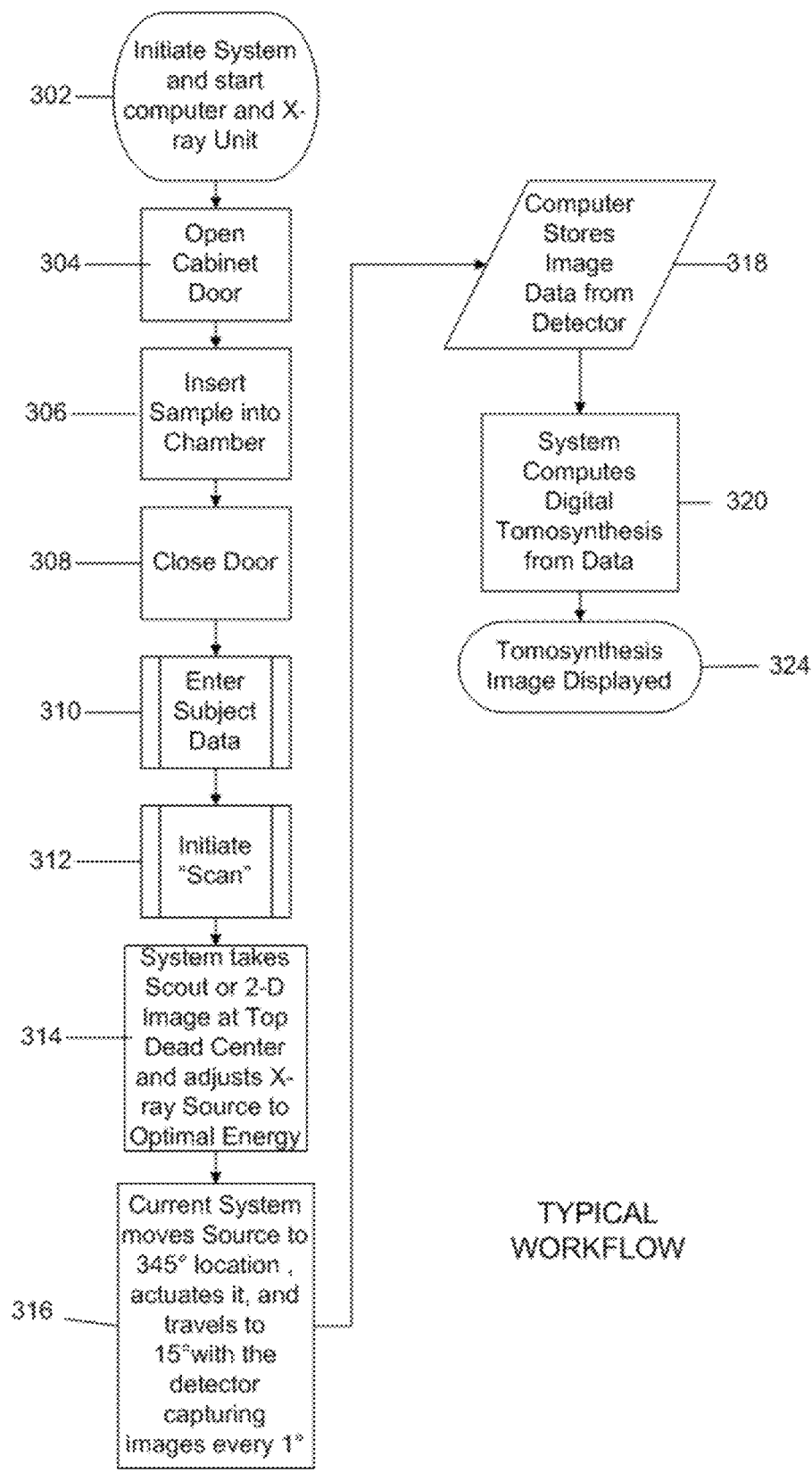
FIG. 3—Displays an exemplary workflow/flowchart of an aspect of the disclosed embodiments.

FIG. 3 illustrates one embodiment of an exemplary workflow from initiating 302 the system 100 through imaging, reconstruction and display 324 of data images collected of the sample 18.

As will be generally understood, the system 100 is initiated 302, the x-ray cabinet door 24 opened 304, and the sample 18 placed into 306 the x-ray cabinet chamber 28. As shown in FIG. 2, for example, the sample 18 is positioned on the detector 20 in a suitable manner. The door 24 is closed 308.

The data and information regarding the sample 18, including any other suitable information or settings relevant to the imaging process and procedure, is entered 310 into the computer 470. The scan is initiated 312. The system 100 will take 314 scout or 2-D images at Top Dead Center, which for purposes of this example is position 14 of FIGS. 1 and 2. The x-ray source 10 can then be moved to other positions, such as positions 12 and 16, and the detector 20 can be used to capture 316 images at various increments along the travel path of the x-ray source 10, such as about every 1 degree.

The captured images are stored 318 and digital tomosynthesis is performed 320. The tomosynthesis image is then displayed 324.

Other embodiments of a system 100 incorporating aspects of the present disclosure are illustrated in FIGS. 1 and 2 where system 100 is totally enclosed or housed in an x-ray cabinet 22 and the x-ray source 10 is stationary relative to the stationary sample, 18 and can be used to obtain a 2-D image. In these embodiments, x-ray source 10 can be positioned at position 14 and the reference "C" refers to the point source of the x-ray beam and the reference "M" refers to the spread or fan of the x-ray beam. While the detector 20 may move or rotate, in accordance with one aspect of the present disclosure, the detector 20 can remain stationary relative to the sample 18 and x-ray source 10 to maintain an equidistant center point. The sample 18 also referred to as the "object" or "imaging object" may be disposed on or rest on the specimen platform 19 (which is a protective cover) or other surface of the detector 20. As with the previous embodiments described herein, the inventive aspects of the present disclosure differ from the prior art in that in prior art systems either the detector and x-ray source 10 and/or the isocenter is above the sample and not at the detector surface. In operation, source 10 is energized to emit an x-ray beam at position 14, located at approximately 0°, and thereby obtain a 2-D image of sample 18. In operation, source 10 is energized to emit an x-ray beam, generally throughout its travel along one or more of the paths or positions described above. The x-ray beam travels through the sample 18 to the detector 16 and to 2-D image is stored. The x-ray source 10 may range from about 0 kVp to about 90 kVp, preferably a 50 kVp 1000 µa x-ray source.

Figure 4:
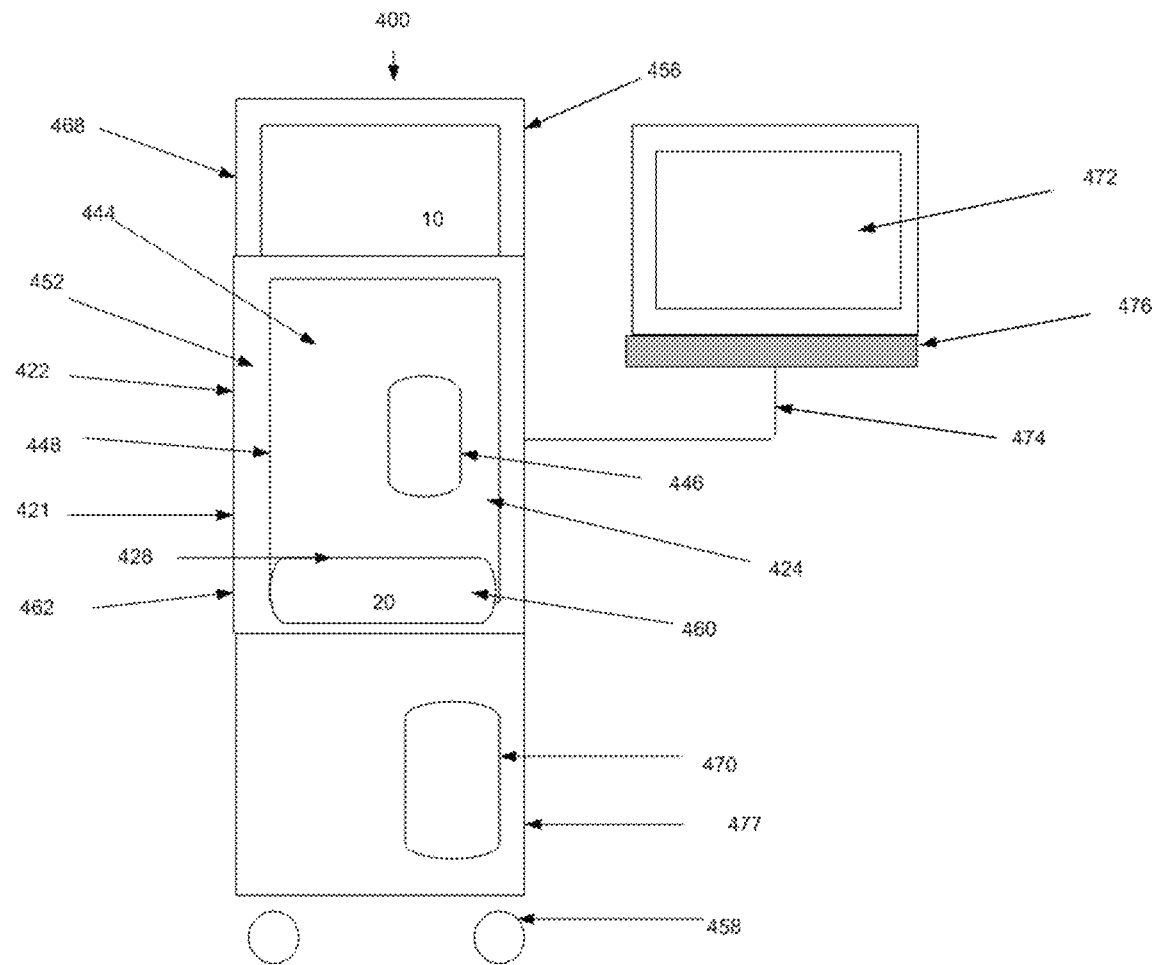
FIG. 4—Displays an example of an x-ray Cabinet System incorporating aspects of the present disclosure.

FIG. 4 shows one embodiment of an x-ray Cabinet System 400 incorporating aspects of the present disclosure that can be used for embodiments with a fixed or moveable x-ray source. In this embodiment, the x-ray Cabinet System 400 is mounted on wheels 458 to allow easy portability. In alternate embodiments, the x-ray Cabinet System 400 can be mounted on any suitable base or transport mechanism. The cabinet 422 in this example, similar to the exemplary x-ray cabinet 22 of FIG. 1, is constructed of a suitable material such as steel. In one embodiment, the cabinet 422 comprises painted steel defining a walled enclosure with an opening or cabinet chamber 428. Within the cabinet chamber 428, behind door 424, resides an interior space forming a sample chamber 444, which in this example is constructed of stainless steel. Access to the sample chamber 444 is via an opening 446. In one embodiment, the opening 446 of the sample chamber 444 has a suitable door or cover, such as a moveable cover 448. In one embodiment, the moveable cover 448 comprises a door which has a window of leaded glass.

Between the outer wall 421 of cabinet 422 and the sample chamber 444 are sheets of lead 452 that serve as shielding to reduce radiation leakage emitted from the x-ray source 10. In the example of FIG. 4, the x-ray source 10 is located in the upper part 456 of the cabinet 422, in the source enclosure 468. The detector 20 is housed in the detector enclosure 460 at an approximate midpoint 462 of the cabinet 422.

Figure 5:
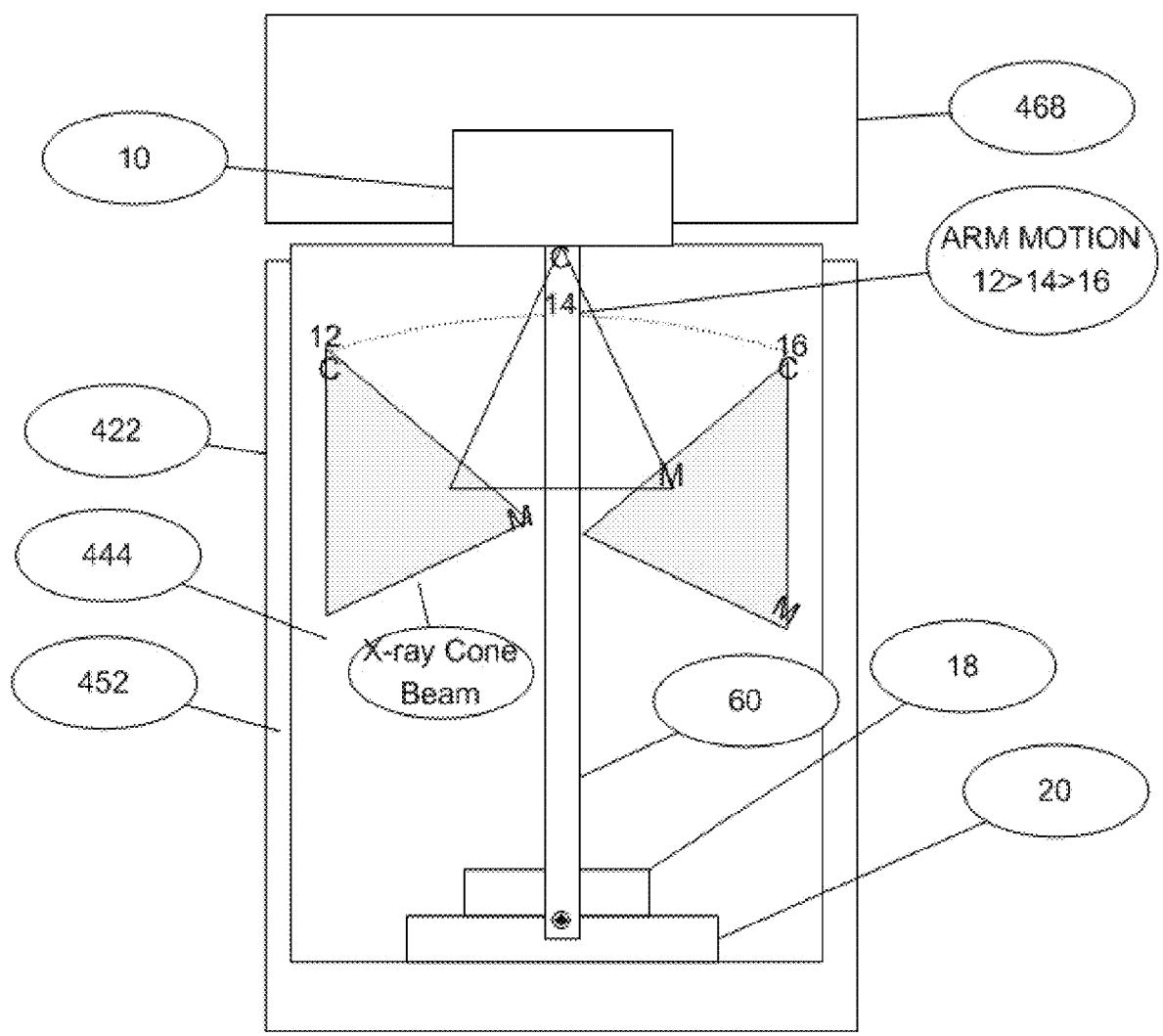
FIG. 5—Displays the sample chamber of the embodiment of FIG. 4 with the swing arm and a detector.
Figure 6:
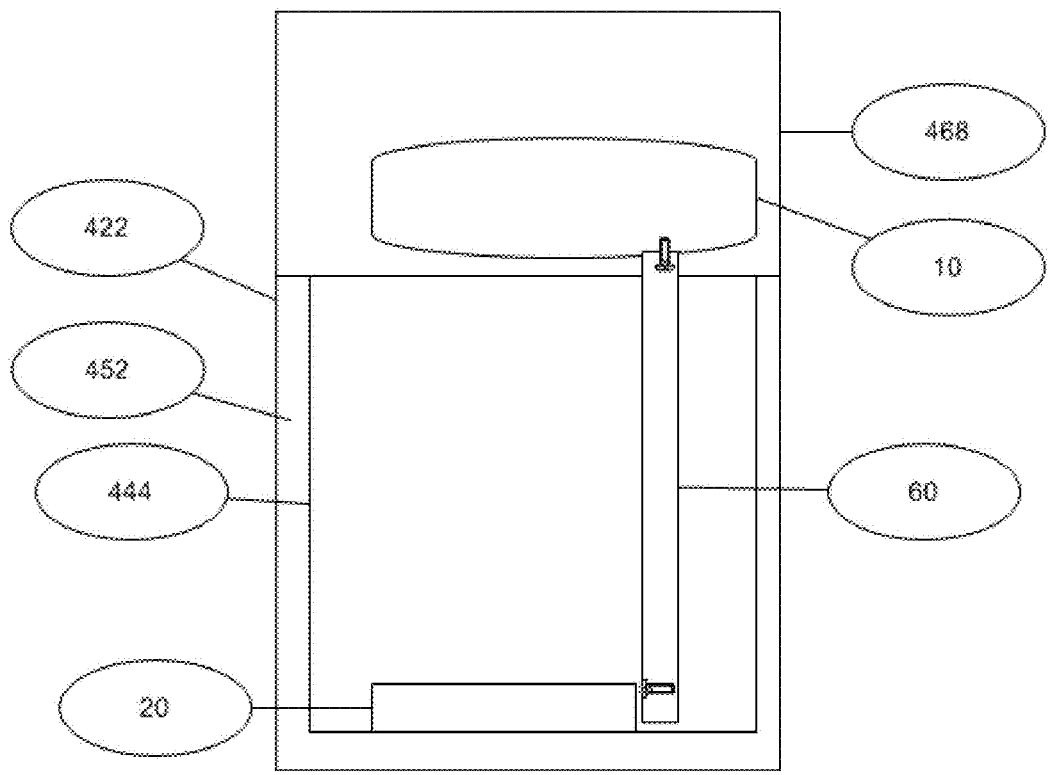
FIG. 6—Displays the lateral view of the x-ray source of the embodiment of FIG. 4 mounted to the top of the swing arm.

In one embodiment, a controller or computer 470 that may be located in an equipment enclosure 477 controls the collection of data from the detector 20, controls the swing arm 60 shown in FIGS. 5 & 6, and x-ray source 10. A monitor 472 displays the compiled data and can, for example, be mounted on an articulating arm 474 that is attached to the cabinet 422. The computer 470 receives commands and other input information entered by the operator via a user interface 476, such as a keyboard and mouse for example. In one embodiment, the computer 470 can comprise a touch screen or near touch screen device. Although the aspects of the disclosed embodiments will generally be described with respect to a computer 470, it will be understood that the computer 470 can comprise any suitable controller or computing device. Such computing devices can include, but are not limited to, laptop computers, mini computers, tablets and pad devices.

The computer 470 can be configured to communicate with the components of the x-ray cabinet system 400 in any suitable manner, including hardwired and wireless communication. In one embodiment, the computer 470 can be configured to communicate over a network, such as a Local Area Network or the Internet.

FIG. 5 shows a front interior view and FIG. 6 shows a lateral interior view of the sample chamber of imaging unit cabinet of FIG. 4. In this embodiment, a sample 18 is placed or otherwise disposed onto the detector 20. Using the computer 470 shown in FIG. 4, the operator enters in the parameters for the scan via the user interface 476, which can be displayed on the monitor 472. As used herein, the term "display" or "monitor" means any type of device adapted to display information, including without limitation CRTs, LCDs, TFTs, plasma displays, LEDs, and fluorescent devices. The computer 470 then sends the appropriate commands to the x-ray source 10 and detector 20 to activate image collection while the swing arm 60 is moving along a path or arc from position 14 to 12 to 16 (which are shown in FIGS. 1 and 5) or vice versa as described, which in this embodiment are at 345°, 0°, and 15° respectively with 0° at top dead center. At the end of the travel of the swing arm 60 at either position 12 or 16, the computer 470 issues the command to the x-ray source 10 and the detector 20 to cease operating. The individual 2-dimensional (2-D) images which were collected, in this example at 1° increments, are then tabulated in the computer 470 to create the tomosynthetic images. In one embodiment, the operator may select which images they wish via the user interface 476 as they are being displayed on the monitor 472. In one embodiment, the devices and components of the x-ray cabinet system 400 are suitably communicatively coupled together, including one or more of hard wire connections or wireless connections using a suitable wireless connection and communication transmission protocol, as will generally be understood. The x-ray cabinet system 400 can also be configured to transfer images via USB, CD-Rom, or WIFI.

The dynamic imaging software of the disclosed embodiments reconstructs three-dimensional images (tomosynthesis) from two-dimensional projection images in real-time and on-demand. The software offers the ability to examine any slice depth, tilt the reconstruction plane for multiplanar views and gives higher resolution magnifications. FIGS. 7A, 7B, and 7C illustrate exemplary images of an apple using the above process.

FIG. 7A is an image of a slice of the apple at it's very top. 59 mm from the bottom. FIG. 7B is an image of an apple computed at 30.5 mm up from the detector, and FIG. 7C is a view of the apple computed at 13.5 mm from the bottom.

The real-time image reconstruction of the present disclosure enables immediate review, higher throughput, and more efficient interventional procedures reducing patient call backs and data storage needs. Multiplanar reconstruction enables reconstruction to any depth, magnification and plane, giving the viewer the greater ability to view and interrogate image data, thereby reducing the likelihood of missing small structures. Built-in filters allow higher in plane resolution and image quality during magnification for greater diagnostic confidence. Software is optimized for performance using GPU Technology.

The reconstruction software used in conjunction with the aspects of the present disclosure provides the users greater flexibility and improved visibility of the image data. It reconstructs images at any depth specified by the user rather than at fixed slice increments. With fixed slice increments, an object located between two reconstructed slices, such as a calcification, is blurred and can be potentially missed. The aspects of the present disclosure provide for positioning the reconstruction plane so that any object is exactly in focus. This includes objects that are oriented at an angle to the detector 20. The aspects of the present disclosure provide for the reconstruction plane to be angled with respect to the detector plane.

In ultrasound-guided breast biopsy, ultrasound imaging is used to help guide the radiologist's instruments to the site of the abnormal growth. An ultrasound-guided breast biopsy can be performed when a breast ultrasound shows an abnormality such as: a suspicious solid mass, a distortion in the structure of the breast tissue and an area of abnormal tissue change. There are times when a physician may decide that ultrasound guidance for biopsy is appropriate even for a mass that can be felt. Ultrasound is the modality of choice for diagnosis of breast cancer in people with dense breasts.

Ultrasound scanners can consist of a console containing a computer and electronics, a video display screen and a transducer that is used to do the scanning. The transducer can be a small hand-held device that resembles a microphone, attached to the scanner by a cord or in this particular embodiment via Bluetooth. The transducer sends out inaudible, high-frequency sound waves into the body and then listens for the returning echoes from the tissues in the body. The principles are similar to sonar used by boats and submarines.

The ultrasound image can be immediately visible on a video display screen that looks like a computer or television monitor. The image is created based on the amplitude (loudness), frequency (pitch) and time it takes for the ultrasound signal to return from the area within the patient that is being examined to the transducer (the device used to examine the patient), as well as the type of body structure and composition of body tissue through which the sound travels. A small amount of gel is put on the skin to allow the sound waves to best travel from the transducer to the examined area within the body and then back again.

FIGS. 8-10 depicts other aspects of embodiments of the present disclosure that include embodiments of ultrasound systems for performing ultrasound imaging on the body of a patient or other subject incorporated into a cabinet x-ray unit. Advantageously, the ultrasound systems operate at relatively low power levels in order to function, thereby enabling the system to take advantage of wireless technologies to un-tether the ultrasound probe from the base unit of the system. This, in turn, provides more flexibility for a clinician or other user of the system and simplifies the ultrasonic procedure.

Aspects of one embodiment are shown in FIG. 8A, that shows an ultrasound system 810, preferably a low power ultrasound system for the reason included herein. As shown, the ultrasound system ("system") 810 generally includes a base unit 812 and probe 814. The base unit 812 may include a processor 816 for performing image processing functions on sonographic data retrieved by the probe 814 during an ultrasonic procedure. FIG. 8A also shows the probe 814 placed adjacent a surface or skin 822 of a body 820 of a patient or other subject. Though understood to be used in applications such as that shown here in FIG. 8A, it is also appreciated that embodiments of the present disclosure may be modified for use with other probe embodiments having different shapes and configurations, including probes configured for penetration into an orifice of the patient, for instance. The base unit 812 may further include a display or monitor 818. Image data processed by the processor 816 of the base unit 812 can be represented as an image on the display 818. The image may be static or continually refreshed during operation of the system 810. Indeed, it is appreciated that the system 810 and its individual components can include additional features and components, though not disclosed herein, while still preserving the principles of the present disclosure. Note also that the base unit 812 can be one of any number devices, including, for example, a dedicated ultrasound device or a dedicated desktop or laptop computer, such as that, for example, computer 470 in FIG. 4. The base unit 812 can also be connected to computer 470 and integrated into x-ray Cabinet System 400. In the presently depicted embodiment, the system 810 implements wireless technology, wherein the base unit 812 and the probe 814 are in two-way, wireless communication with one another. To that end, the base unit 812 includes a base antenna 824 that wireless communicates with a probe antenna 826 included with the probe 814. Wireless signals 828, representing electromagnetic communication such as, for example, RF, WIFI or Bluetooth signals between the base unit 812 and the probe 814, can be used. In this way, sonographic data detected by the probe 814 can be wirelessly transmitted by the probe antenna 826 to the base unit 812 via the base antenna 824 for processing by the processor 816. Coupling of the probe and base unit (including the components thereof) can be accomplished using one or more of hard wire connections or wireless connections using a suitable wireless connection and communication transmission protocol, as will generally be understood. Note that one or more of a variety of wireless data transfer protocols, including Wireless USB, IEEE 802.x, BLUE TOOTH, WIMAX, etc., may be employed for such data transfer as described herein. FIG. 8B represents another possible embodiment, wherein the base unit 812 of ultrasound system 810 that is communicatively coupled with the probe 814 not wirelessly, but via a cable 830. As such, it is appreciated that the ultrasound system as described herein may be employed with a wireless, non-wireless, or even hybrid wireless/cabled communication link between the base unit and the probe.

Various probe embodiments are shown in FIGS. 9 and 9A. Probes such as the embodiments shown, for example in FIG. 9A probe 814 are generally described by the size and shape of their face 942 ("footprint"). Selecting the right probe for the situation can be important to obtain good images, although there may be times where more than one probe may be appropriate for a given exam. In FIG. 9 there are three types of probe used in emergency and critical care point-of-care ultrasound: linear 948, curvilinear 950, and phased array 952. Linear 948 (also sometimes called vascular) probes are generally high frequency sonation 954A, better for imaging superficial structures and vessels, and are also often called a vascular probe. Curvilinear probes 950 may have a wider footprint and lower frequency/sonation 954B for transabdominal imaging, or in a tighter array (wider field of view) and higher frequency for endocavitary imaging. A phased array probe 952 generates an image from an electronically steered beam (e.g., an ultrasound wave) 954C in a close array, generating an image that comes from a point and is good for getting between ribs such as in cardiac ultrasound. Both curvilinear and phased array probes generate sector or "pie-shaped" images, narrower in the near field and wider in the far field, while linear probes typically generate rectangular images on the screen Aspects of another probe embodiment are shown in FIG. 9A, which can include various aspects regarding the probe 814 of the system 810 shown in FIG. 8A. As depicted, the probe 814 according to this embodiment is a wireless probe and includes a probe housing that acts as a covering for various internal components of the probe. A head 942 is included in the probe 814 housed via an ergonomic case/handle/enclosure 940, which may be constructed of plastic or metal or combination thereof, which in turn houses the array of crystals that act as transducers to enable insonation of an object within the body of the patient to be imaged during ultrasound procedures. A location 944 is specified, depicting one possible location for inclusion of an internal probe antenna, such as for example, base antenna 824 enabling wireless communication with the base unit 812 as generally depicted in FIG. 8A or one possible location for inclusion of a cable connector that could act as a connection location for cable 830 as generally depicted in FIG. 8B. A location 946 is also designated for the inclusion of various buttons (not shown) that enable clinician control of the probe 814 and the base unit 812 during ultrasound procedures. Thus, it is appreciated that the probe 814 as shown in FIG. 9A can be desirably included within the sterile field of a patient undergoing an ultrasound procedure in preparation for receiving an intravenous catheter, such as a PICC line, for instance. Note that the particular design of the probe 814 as shown in FIG. 9A, can be varied such that the size, look, and configuration of the probe may be modified as shown in the embodiment shown in FIG. 9, for example.

Aspects of another embodiment is shown in FIG. 8C that includes a cabinet system 400 with base unit 812 which may be positioned in an equipment enclosure 477 of the cabinet system 400 along with computer 470. Base unit 812 can include processor 816 and display 818 is display driver. In this embodiment, base unit 812 can include base antenna 824 as shown in FIG. 8A or can be hard wire connected to the connection point 830A. Connection point 830A can, in turn, be a cable connector for the cable 830 for ultrasound probe 814 in FIG. 8B or an antenna similar to base antenna 824 for ultrasound probe 814 in FIG. 8A. Base unit 812 in FIG. 8C, can be connected through display 818 when it is a display driver directly to monitor 472 or indirectly to monitor 472 when the display driver is connected to computer 470.

Figure 10C:
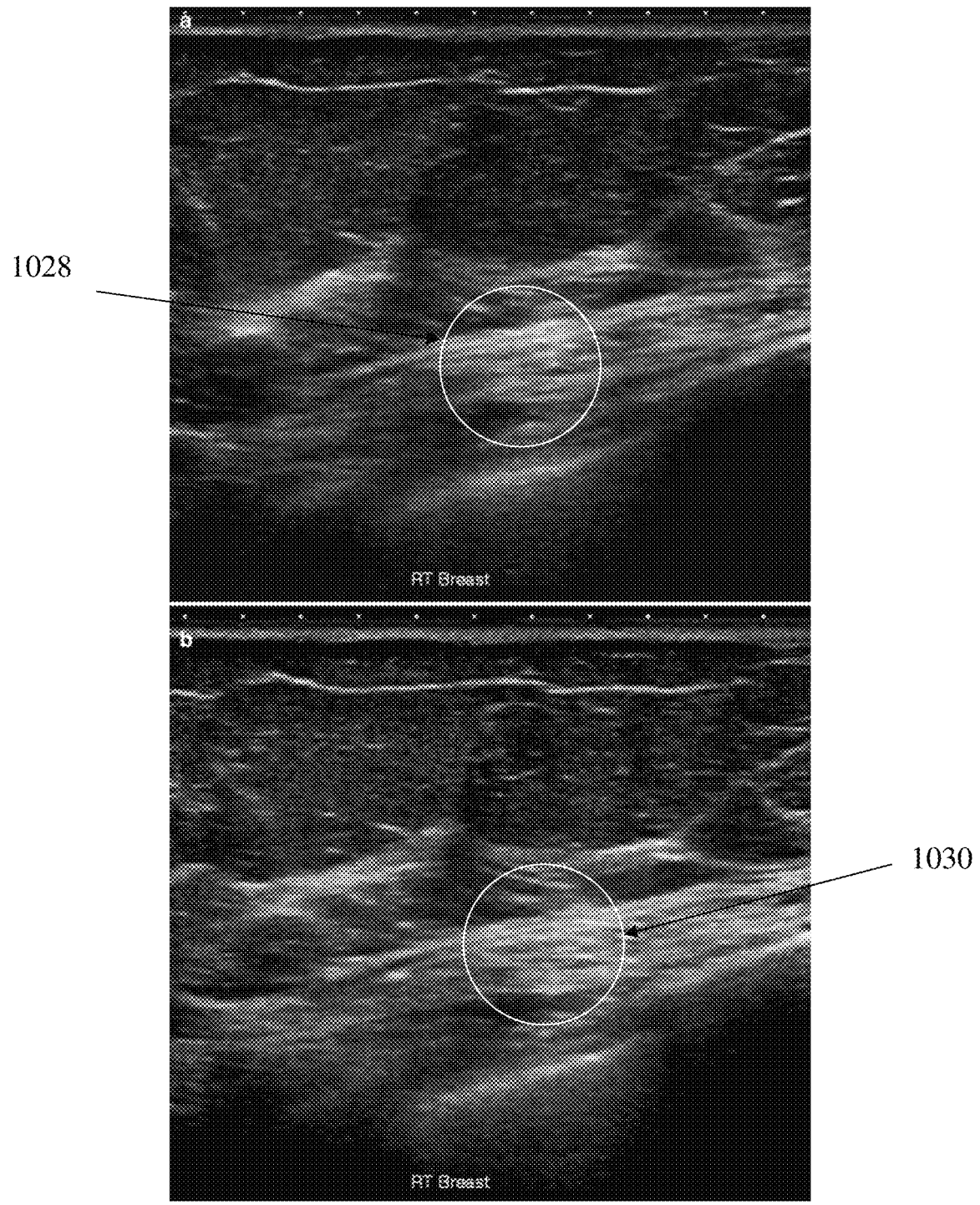

As shown in FIGS. 10A1 and 10A2, the probes send an ultrasound wave and receive resulting sonographic signals that are transmitted to the base unit. The sonographic signals include sonographic data that is processed by the processor 816 to form a shaped and focused ultrasound image of the insonated object FIGS. 10A, 10B, 10C. 10A exhibits the technique utilized to image a breast 1002. For example, the wired 830 linear probe 948 emits an ultrasound signal 954A in different quadrants, 1004, 1006, 1008, 1010 as the probe 948 is moved to the quadrants, 1004, 1006, 1008, 1010 to ensure complete examination of the breast 1002.

FIG. 10Ba shows a breast sonation with highlight of pulmonary blood flow 1020 and ductual plug/restriction 1022 within the breast and 10Bb shows a graphical quantity of bloodflow. The top graphic 1024 exhibits the pulmonary flow 1020 and the bottom graphic 1026 shows the restricted flow from the ductal plug/restriction 1022. FIG. 10Ca shows a dense area 1028 in the breast sonation and 10Cb shows calcifications 1030 within the breast FIG. 10D includes an embodiment that can include the display of both a radiographic image 1014 of the breast 1002 versus a sonation image 1016 of the same breast. A radiographic image and a sonation image obtained through ultrasound are each capable of displaying different features or pathology of the same specimen. Examples of such specimen features or pathology that can be shown in a radiographic image but not a sonation image include calcificiations and hard structures. Examples of such specimen features or pathology that can be shown in a sonation image but not in a radiographic image include features composed of water/liquid. All of the above ultrasound components, in this embodiment, can be incorporated into a cabinet x-ray unit FIG. 4 with 400 incorporating unit 810, FIG. 9A and displaying the sonation as previously mentioned in FIG. 8A—818 in components FIG. 4—470, 472, 474, 476.

Benefits to an integration of x-ray imaging and ultrasound can include, for example, a smaller equipment footprint in the cramped space of most operating rooms and the simultaneous access to display the image data from both image procedures to quickly and efficiently provide such access to, for example, a physician in a surgical setting where time is of the essence when performing such procedures. Specifically, for example, it would be advantageous with the close quarters in breast procedure rooms to create a system and method incorporating 2 modalities utilized in breast intervention procedures for the diagnosis and verification for breast cancer. Systems for specimen radiography assist radiologists and surgeons in the detection and classification of abnormal lesions in medical images gleaned from breast biopsies/lumpectomies and an ultrasound-guided system uses sound waves to help locate a lump or abnormality and perform breast interventional procedures. It is less invasive than surgical biopsy, leaves little to no scarring and does not involve exposure to ionizing radiation. With the utilization of a dual modality machine, the physician can detect the abnormalities, remove the abnormalities, and verify that they have achieved a clean margin, currently 1 mm, from the cancerous or abnormal tissues. Currently it is believed that there is not a system or method utilizing both Ultrasound and Radiography in a cabinet system.

Thus, while there have been shown and described and pointed out fundamental novel features of the invention as applied to the exemplary embodiments thereof, it will be understood that various omissions and substitutions and changes in the form and details of devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the present disclosure may be incorporated in any other disclosed or described or suggested form or embodiment as a general matter of design choice. It is the intention, therefore, to be limited only as indicated by the scope of the claims appended hereto.

Aspects of the present disclosure may be embodied in other specific forms without departing from its spirit or essential characteristics. The described embodiments are to be considered in all respects only as illustrative, not restrictive. All changes that come within the meaning and range of equivalency of the claims are to be embraced within their scope.

What is claimed is:

1. A cabinet x-ray and ultrasound system for obtaining x-ray images and ultrasound images of a specimen, the system comprising:
    a cabinet comprises a walled enclosure surrounding an interior chamber, a door configured to cover the interior chamber and a sampling chamber within the interior chamber for containing the specimen;
    a display;
    an x-ray system including:
        an x-ray source;
        an x-ray detector;
        a specimen platform; and
        a controller configured to:
            selectively energize the x-ray source to emit x-rays through the specimen to the x-ray detector;
            control the x-ray detector to collect a projection x-ray image of the specimen when the x-ray source is energized; and
            selectively display the x-ray image on the display; and
    an ultrasound system including:
        a probe configured to transmit an ultrasound wave and receive sonographic data in response to the transmitted ultrasound wave; and
        an ultrasound base unit in communication with the probe and including a processor, the processor configured to receive the sonographic data from the probe and perform image processing functions on sonographic data to collect an ultrasound image and selectively display the ultrasound image on the display.

2. The cabinet x-ray and ultrasound system of claim 1, wherein the specimen platform is configured for excised tissue, organ or bone specimens.

3. The cabinet x-ray and ultrasound system of claim 1, wherein the specimen platform is configured for any organic or inorganic specimen that fits inside an x-ray cabinet.

4. The cabinet x-ray and ultrasound system of claim 1, further comprising:
    the specimen platform having a protective cover of and in physical contact with the x-ray detector;
    a motion control mechanism configured for moving the x-ray source to or along a plurality of positions within the interior chamber relative to the specimen disposed on the specimen platform; and
    a controller further configured to:
        selectively energize the x-ray source to emit x-rays through the specimen to the x-ray detector at selected positions of the x-ray source relative to the specimen such that the isocenter of the emitted x-rays at the selected positions is located at a surface of the x-ray detector;
        control the x-ray detector to collect projection x-ray images of the specimen when the x-ray source is energized at the selected positions, wherein one of the projection x-ray images is a two-dimensional x-ray image taken at standard imaging angle of approximately 0°;
        create a tomosynthetic x-ray image reconstructed from a collection of projection x-ray images;
        process the collection of the projection x-ray images in the controller into one or more reconstructed tomosynthetic x-ray images representing a volume of the specimen and relating to one or more image planes that are selectively the same or different from that of the two-dimensional x-ray image; and
        selectively display the two-dimensional x-ray image and the one or more reconstructed tomosynthetic x-ray images.

5. The cabinet x-ray and ultrasound system of claim 1, wherein the probe and ultrasound base unit are in two-way communication with one another.

6. The cabinet x-ray and ultrasound system of claim 1, wherein the probe and ultrasound base unit are in communication via at least one of a cable or a wireless system.

7. The cabinet x-ray and ultrasound system of claim 1, wherein the ultrasound base unit also includes a display driver that is configured to receive the ultrasound image from the processor and send it to the controller, the controller configured to selectively display the ultrasound image on the display.

8. The cabinet x-ray and ultrasound system of claim 1, wherein the x-ray image and the ultrasound image are concurrently displayed.

9. A cabinet x-ray and ultrasound system for obtaining x-ray images, projection x-ray images, reconstructed tomosynthetic x-ray images and ultrasound images of a specimen, the system comprising:
    a cabinet comprises a walled enclosure surrounding an interior chamber, a door configured to cover the interior chamber, a sampling chamber within the interior chamber for containing the specimen and an equipment enclosure;
    a display;
    an x-ray system including:
        an x-ray source positioned in the interior chamber;
        an x-ray detector positioned in the interior chamber;
        a specimen platform positioned in the interior chamber and which is a protective cover of and in physical contact with the x-ray detector;
        a motion control mechanism positioned in the interior chamber and configured for moving the x-ray source to or along a plurality of positions within the interior chamber relative to the specimen disposed on the specimen platform; and
        a controller positioned in the equipment enclosure and configured to:
            selectively energize the x-ray source to emit x-rays through the specimen to the x-ray detector at selected positions of the x-ray source relative to the specimen such that the isocenter of the emitted x-rays at the selected positions is located at a surface of the x-ray detector;

control the x-ray detector to collect a projection x-ray images of the specimen when the x-ray source is energized at the selected positions, wherein one of the projection x-ray images is a two-dimensional x-ray image taken at standard imaging angle of approximately 0°;

create a tomosynthetic x-ray image reconstructed from a collection of projection x-ray images;

process the collection of the projection x-ray images in the controller into one or more reconstructed tomosynthetic x-ray images representing a volume of the specimen and relating to one or more image planes that are selectively the same or different from that of the two-dimensional x-ray image; and selectively display the two-dimensional x-ray image on the display and the one or more reconstructed tomosynthetic x-ray images; and an ultrasound system including:
a probe configured to transmit an ultrasound wave and receive sonographic data in response to the transmitted ultrasound wave; and an ultrasound base unit positioned in the equipment enclosure and in communication with the probe and including a processor and a display driver, the processor configured to receive the sonographic data from the probe and perform image processing functions on sonographic data to collect an ultrasound image, the display driver configured to receive the ultrasound image from the processor and send it to the controller, the controller configured to selectively display the ultrasound image on the display.

10. The cabinet x-ray and ultrasound system of claim 9, wherein the specimen platform is configured for excised tissue, organ or bone specimens.

11. The cabinet x-ray and ultrasound system of claim 9, wherein the specimen platform is configured for any organic or inorganic specimen that fits inside an x-ray cabinet.

12. The cabinet x-ray and ultrasound system of claim 9, wherein the probe and ultrasound base unit are in two-way communication with one another.

13. The cabinet x-ray and ultrasound system of claim 9, wherein the probe and ultrasound base unit are in communication via at least one of a cable or a wireless system.

14. A method for obtaining an x-ray image and an ultrasound image of a specimen in a cabinet x-ray and ultrasound system, processing and displaying the x-ray image and ultrasound image of the specimen, wherein the cabinet x-ray and ultrasound system comprises:
a cabinet defining an interior chamber;
a display;
an x-ray system including:
an x-ray source;
an x-ray detector;
a specimen platform having a protective cover of and in physical contact with the x-ray detector;
a motion control mechanism configured for moving the x-ray source to or along a plurality of positions within the interior chamber relative to the specimen disposed on the specimen platform; and
a controller configured to:
selectively energize the x-ray source to emit x-rays through the specimen to the x-ray detector at selected positions of the x-ray source relative to the specimen such that the isocenter of the emitted x-rays at the selected positions is located at a surface of the x-ray detector;

control the x-ray detector to collect a-projection x-ray images of the specimen when the x-ray source is energized at the selected positions, wherein one of the projection x-ray images is a two-dimensional x-ray image taken at standard imaging angle of approximately 0°;

create a tomosynthetic x-ray image reconstructed from a collection of projection x-ray images;

process the collection of the projection x-ray images in the controller into one or more reconstructed tomosynthetic x-ray images representing a volume of the specimen and relating to one or more image planes that are selectively the same or different from that of the two-dimensional x-ray image; and selectively display the projection x-ray images and the one or more reconstructed tomosynthetic x-ray images on the display; and an ultrasound system including:
a probe configured to transmit an ultrasound wave and receive sonographic data in response to the transmitted ultrasound wave; and an ultrasound base unit in communication with the probe and including a processor, the processor configured to receive the sonographic data from the probe and perform image processing functions on sonographic data to collect an ultrasound image and selectively display the ultrasound image on the display, wherein the method comprises:

controlling the x-ray detector to collect projection x-ray images of the specimen when the x-ray source is energized at the selected positions such that the isocenter of the emitted x-rays at the selected positions is located at a surface of the x-ray detector, wherein one of the projection x-ray images is a two-dimensional x-ray image taken at standard imaging angle of approximately 0°;

controlling the ultrasound system to transmit an ultrasound wave and receive sonographic data in response to the transmitted ultrasound wave and processing the sonographic data to collect an ultrasound image;

creating a tomosynthetic x-ray image reconstructed from a collection of projection x-ray images;

processing the collection of the x-ray images in the controller into one or more reconstructed tomosynthetic x-ray images representing a volume of the specimen and relating to one or more image planes that are selectively the same or different from that of the two-dimensional x-ray image; and selectively displaying at least one of the following: at least one of the projection x-ray images, the one or more reconstructed tomosynthetic x-ray images and the ultrasound image on the display.

15. The method of claim 14, comprising concurrently displaying at least one of the projection x-ray images and the ultrasound image.

16. The method of claim 14, comprising concurrently displaying at least two of the projection x-ray images, the one or more reconstructed tomosynthetic x-ray images and the ultrasound image.

* * * * *